US00PP20833P2

(12) United States Plant Patent
Bradford

(10) Patent No.: US PP20,833 P2
(45) Date of Patent: Mar. 16, 2010

(54) PLUM TREE NAMED 'AUGUST MAJESTY'

(50) Latin Name: *Prunus salicina*
Varietal Denomination: August Majesty

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,599

(22) Filed: Dec. 15, 2008

(51) Int. Cl.
*A01H 5/00* (2006.01)

(52) U.S. Cl. ..... Plt./184

(58) Field of Classification Search ..... Plt./184, Plt./180
See application file for complete search history.

(56) References Cited

U.S. PATENT DOCUMENTS

PP14,247 P2 10/2003 Bradford

*Primary Examiner*—June Hwu

(57) ABSTRACT

The present invention relates to a plum tree and more particularly to a new and distinct variety broadly characterized by a medium size, vigorous, hardy, and moderately productive tree. Being self-unfruitful, the present variety requires cross pollination from a plum that blooms during the mid to late season. The fruit matures under the ecological conditions described during mid August, with first picking on Aug. 14, 2008. The fruit is uniformly large in size, dark purplish red in skin color, freestone in type, globose in shape, light greenish yellow in flesh color, firm in texture, and sweet in flavor.

1 Drawing Sheet

Botanical classification: *Prunus salicina.*
Varietal denomination: 'August Majesty'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'August Majesty'.

During a typical blooming season I isolate as seed parents both individual and groups of different plum trees by covering them with screen houses. A hive of bees is placed inside each such house, and bouquets to provide pollen from different plum trees are placed in buckets near the trees approximately every two days for the duration of the bloom. During 2001 one such house containing a group of five different plum trees was crossed by me in this manner. To pollinate the plum trees in this house, I selected bouquets from several sources of plum trees without keeping specific written details. Upon reaching maturity the fruit from these plum trees was harvested and the seeds were removed, cracked, stratified and germinated as a group with the label "H8". They were grown as seedlings on their own root in my greenhouse and upon reaching dormancy transplanted to a cultivated area of my experimental orchard located near Le Grand, Calif. in Merced County (San Joaquin Valley). During the summer of 2005 the claimed variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects.

The reproduction of the variety included the use of 'Nemaguard' (unpatented) rootstock upon which the present variety was true to type.

The present variety is similar to 'August Yummy' (U.S. Plant Pat. No. 14,247) plum by being self-unfruitful and by producing fruit that is sweet in flavor, firm in texture, dark red in color, and that ripens in mid August, but is distinguished therefrom by producing fruit that is almost purely globose instead of oblate in shape, that is freestone instead of clingstone, that is somewhat larger in size, and that is not as prone to yellow or green areas on the shoulders where sun protected.

SUMARY OF VARIETY

The present plum variety is characterized by a medium size, vigorous, hardy, and moderately productive tree. Being self-unfruitful, the present variety requires cross pollination from a plum that blooms during the mid to late season. The fruit matures under the ecological conditions described during mid August, with first picking on Aug. 14, 2008. The fruit is uniformly large in size, dark purplish red in skin color, freestone in type, globose in shape, light greenish yellow in flesh color, firm in texture, and sweet in flavor.

DRAWING

The accompanying photograph consists of a three inset pictures of typical fruit to display the characteristics of the skin color and form with one half fruit sectioned to reveal the flesh and stone, typical leaves, a dry stone, and one inset depicting the flower buds and blossoms as they appeared on the tree during the blooming season.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Aug. 18, 2008, on the original tree during its seventh growing season. The flower and bud descriptions were developed during the previous blooming season. All major color code designations are by reference to the Inter-Society Color Council, National Bureau of Standards. Common color names are also used occasionally.

Parentage

Seed parent: Unknown.
Pollen parent: Unknown.

Tree

Size: Medium, reaching and maintaining a height of 12' [3.66 m.] and a spread of 8' [2.44 m.] after seven growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Moderately productive, thinning usually necessary.

Fertility: Self-unfruitful, requiring cross pollination by a suitable mid to late seasonal blooming plum such as 'September YUMMY' (U.S. Plant Pat. No. 14,220).

Bearing: Regular bearing observed thus far, weather dependent.

Trunk:

*Size.*—Medium, reaching a maximum diameter of 5" [127 mm.] after the seventh growing season.

*Texture.*—Medium shaggy.

*Bark color.*—A Dark yellowish brown [78. d.yBr] and Moderate reddish brown [43. m.rBr] variegation with Dark orange yellow [72. d.OY] crevices present.

*Lenticels.*—Approximate Number Per Square Inch: 5. Color: Brownish orange [54. brO]. Average Size: 3/8" [9.5 mm.]. Shape: Eye-shaped, elongated.

Branches:

*Size.*—Diameter of central leader 2¾" [70 mm.] measured 12" above the first lateral, which itself has a maximum diameter of 1¾" [45 mm.].

*Texture.*—Smooth on first and second year wood, increasing roughness with age.

*Color.*—1st Year Wood Topside: Strong yellowish brown [74. s.yBr]. 1st Year Wood Underside: Strong yellow green [117. s.YG]. Older Wood: Strong yellowish brown [77. s.yBr].

*Lenticels.*—Number Per Square Inch: More than 40 on second year wood. Color: Light orange yellow [70. l.OY]. Average Size: 1/16" [1.6 mm.]. Shape: Eye-shaped, elongated.

Leaves:

*Size.*—Medium. Average Length: 4¼" [108 mm.]. Average Width: 1⅝" [41 mm.].

*Arrangement.*—Alternate.

*Thickness.*—Medium.

*Form.*—Elliptical.

*Apex.*—Acuminate.

*Base.*—Acute with an average angle base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG].

*Stipules.*—Number: Up to 2 per leaf, up to 6 per growing tip. Average Length: 5/16" [7.9 mm.]. Color: Moderate yellow green [120. m.YG] becoming Dark yellowish brown [78. d.yBr] with age.

*Glands.*—Number: 1 to 4 per leaf, mostly 2. Position: Alternately and oppositely positioned just below the intersection of the petiole and the leaf blade. Size: Small. Form: Globose. Color: Light yellow green [119. l.YG] becoming Dark brown [59. d.Br] in the center with age.

*Leaf buds.*—Pointed, medium.

Flower buds:

*Hardiness.*—Hardy, with respect to central California winters.

*Diameter.*—Typically 3/16" [4.8 mm.] 1 week before bloom.

*Length.*—Typically 3/8" [9.5 mm.] 1 week before bloom.

*Form.*—Not appressed.

*Surface.*—Pubescent.

*Tip color.*—White [263. White].

Flowers: Perfect, complete, perigynous, usually a single pistil, about thirty stamens, five sepals and petal locations alternately positioned.

*Average flower diameter.*—1" [25.4 mm.].

*Number of petals.*—Five, no double blossoms observed.

*Petal shape.*—Oval to circular.

*Petal margin.*—Entire, smooth to slightly wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Strong orange [50. s.O] over Brilliant yellow [83. brill.Y].

*Stigma color.*—Brilliant greenish yellow [98. brill.gY].

*Sepal color.*—Brilliant yellow green [116. brill.YG] on the outer surface with Grayish yellowish pink [32. gy.ypk] toward the edges.

*Sepal length.*—3/16" [4.8 mm.].

*Sepal width.*—⅛" [3.2 mm.].

*Sepal apex.*—Rounded to elliptical to match the width and length.

*Sepal margin.*—Fairly smooth with slight serrations toward the apex.

*Average pistil length.*—9/16" [14.3 mm.].

*Average stamen length.*—7/16" [11.1 mm.].

*Fragrance.*—Moderate.

*Bloom density.*—Heavy.
*Number per cluster.*—2 to 10, average 5.
*Pollen production.*—Medium, average enticement to bees.
*Blooming period.*—Medium to late, with 'Santa Rosa' plum (unpatented).
*Onset of bloom.*—One percent on Feb. 27, 2008.
*Date of full bloom.*—Mar. 8, 2008.
*Duration of bloom.*—One to two weeks, dependent on ambient temperature.

FRUIT

Maturity when described: Firm ripe, Aug. 18, 2008.
Date of first picking: Aug. 14, 2008.
Date of last picking: Aug. 24, 2008.
Size: Uniform, large.
*Average diameter axially.*—2¾" [69.9 mm.].
*Average diameter across cheek plane.*—2⅞" [73.0 mm.].
*Average diameter across suture plane.*—2 13/16" [71.5 mm.].
*Typical Weight.*—7.4 ounces [210 grams].
Form: Uniform, globose, symmetrical.
*Longitudinal section form.*—Round.
*Transverse section through axial diameter.*—Round.
Suture: A very shallow trough extending from the base to the apex, slightly sharper toward both the base and apex.
Ventral surface: Rounded, slightly lipped toward the base.
Lips: Equal.
Cavity: Circular to somewhat elongated in the suture plane, suture showing on one side, stem indentations occur occasionally.
*Depth.*—7/16" [11.1 mm.].
*Breadth.*—1¼" [31.8 mm.].
Base: Rounded to slightly truncate.
Apex: Rounded, some with a slight protrusion.
Pistil point: An inconspicuous Grayish yellowish brown [80. gy.yBr] dot located at the end of the suture.
Stem: Medium.
*Average length.*—7/16" [11.1 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Slight in dry season.
*Color.*—Deep purplish red [256. deep pR] over a Deep red [13. deep R] background the slightest amount of Light grayish reddish brown [45. l.gy.rBr] freckling throughout.
*Bloom.*—Abundant.
Flesh:
*Color.*—Pale greenish yellow [104. p.gY].
*Surface of pit cavity.*—Covered with Pale yellow [89. p.Y] fibers.
*Amygdalin.*—Slight.
*Juice.*—Moderate, rich.
*Texture.*—Firm, meaty.
*Fibers.*—Abundant, fine, tender.
*Ripens.*—Slightly earlier toward the apex.
*Flavor.*—Sweet with moderate acid, typically 18 brix.
*Aroma.*—Moderate.
*Eating quality.*—Very good.

STONE

Type: Freestone.
Form: Oval.
Hilum: Narrow.
Base: Straight, truncate.
Apex: Rounded with a sharp 3/32" [2.4 mm.] tip.
Sides: Equal.
Surface: Rough throughout, a vertical ridge on each side of the dorsal fin, another vertical ridge on each side closer to the ventral edge, a flat fin protruding on the ventral edge toward the apex.
External color of stone: Brownish orange [54. brO] when dry.
Pit wall color when cracked: Light orange yellow [70. l.OY].
Cavity surface color: Light orange yellow [70. l.OY].
Average pit wall thickness: 3/32" [2.4 mm.].
Average width: 11/16" [17.5 mm.].
Average length: 15/16" [23.8 mm.].
Average breadth: ½" [12.7 mm.].
Tendency to split: Slight.
Kernel:
*Form.*—Oval.
*Skin color.*—Moderate yellow [87. m.Y].
*Pellicle color.*—Grayish yellowish brown [80. gy.yBr].
*Vein color.*—Dark yellowish brown [78. d.yBr].
*Taste.*—Bitter.
*Viable.*—Yes.
*Average width.*—½" [12.7 mm.].
*Average length.*—9/16" [14.3 mm.].
*Amygdalin.*—Moderate.

Use

Market: Fresh market and long distance shipping.
Keepinq quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is similar to 'August Yummy' (U.S. Plant Pat. No. 14,247) plum by being self-unfruitful and by producing fruit that is sweet in flavor, firm in texture, dark red in color, and that ripens in mid August, but is distinguished therefrom by producing fruit that is almost purely globose instead of oblate in shape, that is freestone instead of clingstone, that is somewhat larger in size, and that is not as prone to yellow or green areas on the shoulders where sun protected.

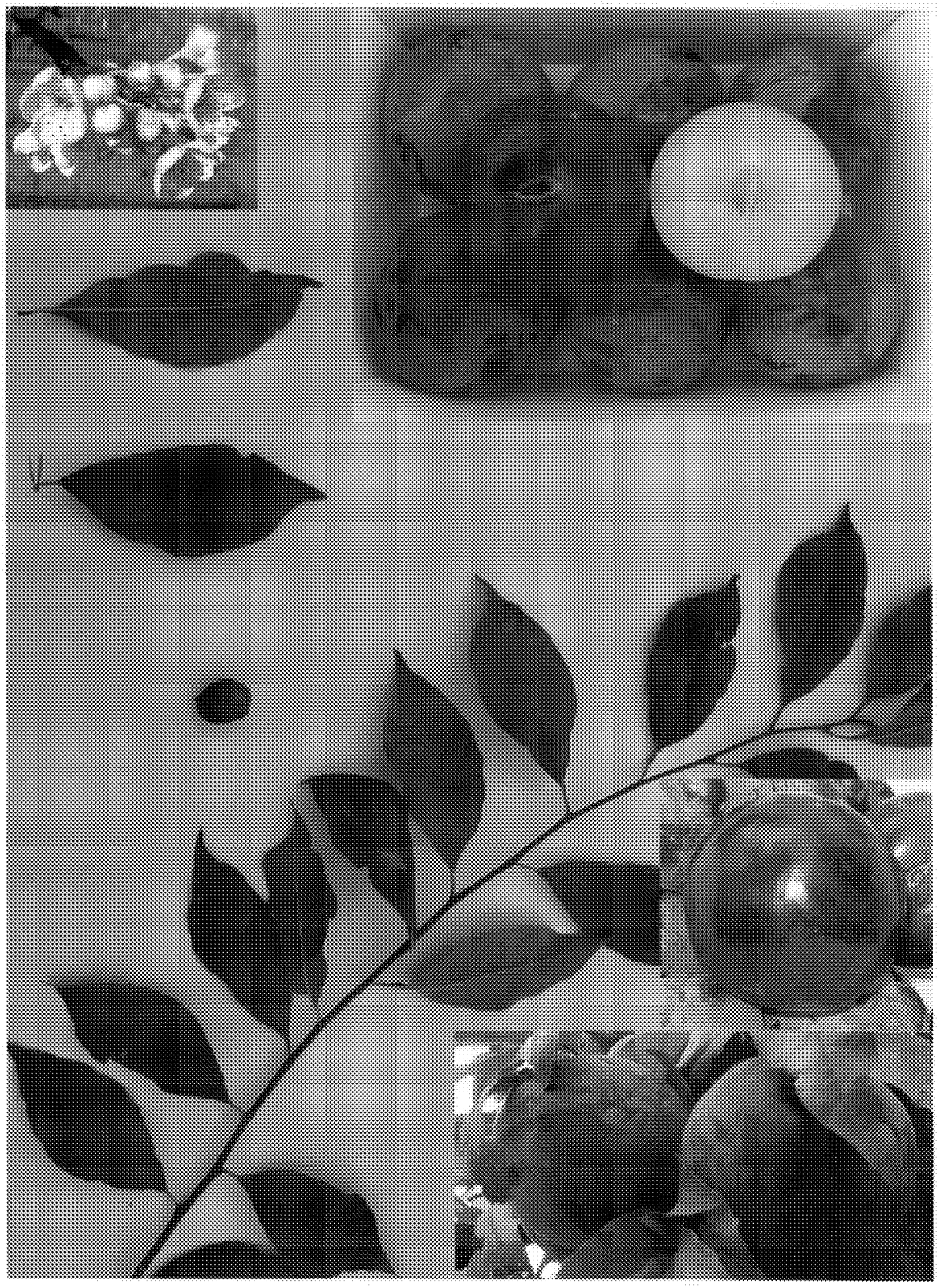

* * * * *